(12) United States Patent
Battle et al.

(10) Patent No.: US 10,650,521 B2
(45) Date of Patent: May 12, 2020

(54) CLASSIFICATION BY MEANS OF RECORDINGS

(71) Applicant: Siemens Healthcare GmbH, Erlangen (DE)

(72) Inventors: Xavier Battle, Forchheim (DE);
Philipp Hoelzer, Bubenreuth (DE);
Bernhard Schmidt, Fuerth (DE);
Grzegorz Soza, Heroldsberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 142 days.

(21) Appl. No.: 15/935,599

(22) Filed: Mar. 26, 2018

(65) Prior Publication Data
US 2018/0286046 A1 Oct. 4, 2018

(30) Foreign Application Priority Data

Mar. 28, 2017 (EP) ..................................... 17163292

(51) Int. Cl.
*G06T 7/00* (2017.01)
*G16H 30/40* (2018.01)

(52) U.S. Cl.
CPC .......... *G06T 7/0016* (2013.01); *G06T 7/0012* (2013.01); *G16H 30/40* (2018.01); *G06T 2207/10072* (2013.01); *G06T 2207/20081* (2013.01)

(58) Field of Classification Search
CPC ... G06T 7/0012; G06T 7/0014; G06T 7/0016; G06T 2207/20081; G06K 9/6217; G06K 9/6218; G06K 9/6229; G16H 30/40; G16H 50/20
See application file for complete search history.

(56) References Cited

U.S. PATENT DOCUMENTS

| 5,868,669 A | 2/1999 | Iliff ............................... 600/300 |
| 2012/0041911 A1* | 2/2012 | Pestian et al. ......... G06N 20/00 706/12 |

OTHER PUBLICATIONS

Kubat, Miroslav :"An Introduction to Machine Learning"; Springer International Publishing; table of contents & preview pages; 2017; ISBN: 978-3-319-63913-0; doi: 10.1007/978-3-319-63913-0.
Jordan, M. I. et al.: "Machine learning: Trends, perspectives, and prospects"; in: Science; vol. 349; Issue 6245; pp. 255-260; Jul. 2015; DOI: 10.1126/science.aaa8415.

(Continued)

*Primary Examiner* — Andrew W Johns
(74) *Attorney, Agent, or Firm* — Harness, Dickey & Pierce, P.L.C.

(57) ABSTRACT

A method is for classifying an examination object by way of recordings. In an embodiment, the method includes capturing at least one optical recording of the examination object; determining and quantifying a number of defined characteristics of the examination object based upon an analysis of the optical recordings with the aid of a machine learning method; and affecting the classification of the examination object in respect of a classification criterion, based upon the quantified characteristics with the aid of a machine learning method. Also described are a classification entity and a medical imaging modality.

26 Claims, 3 Drawing Sheets

(56) References Cited

OTHER PUBLICATIONS

Husarik D. et al: "Assessment of digital clubbing in medical inpatients by digital photography and computerized analysis"; Swiss medical weekly; pp. 132-138; 2002; XP055383374; Switzerland; Found in the Internet: URL:https://smw.ch/en/resource/jf/journal/file/view/article/smw.2002.09907/smw.2002.09907.pdf/ [found on Jun. 20, 2017].

Arulmozhi A. et al: "GA Based Feature Ranking Mechanism to Detect New Born Infants Jaundice With an Ensemble Tree Strategy"; Journal of Theoretical and Applied Information Technology; vol. 65 No. 3; pp. 881-889, XP055382928; ISSN: 1992-8645.

Wadhawan, Tarun et al.: "SkinScan (c) : A portable library for melanoma detection on handheld devices"; 2011; 8th IEEE International Symposium on Biomedical Imaging: From Nano to Macro; IEEE United States; pp. 133-136; XP031944505; DOI: 10.1109/ISBI.2011.5872372; ISBN: 978-1-4244-4127-3.

Goodfellow, Ian et al.: "Deep Learning"; Overview; MIT Press; 2016; ISBN: 9780262337434; accessible online at: http://www.deeplearningbook.org/.

Mustain Billah et al: "An Early Diagnosis System for Predicting Lung Cancer Risk Using Adaptive Neuro Fuzzy Inference System and Linear Discriminant Analysis"; Journal of MPE Molecular Pathological Epidemoiology; Bd. I Nr. 1:3; 1-4; XP055382924;.

German Office Action dated Jun. 6, 2017, for Application No. EP17163292.0.

Bai Nina et al: "Distinguishing Between Dementia and Depression with Neuroimaging", UCSF—University of California San Francisco, XP055643854;: URL:https://www.ucsf.edu/news/2017/03/406066/distinguishing-between-dementia-and-depression-neuroimaging; [gefunden am Nov. 19, 2019]; 2017.

Zhu Yu et al: "Automated Depression Diagnosis Based on Deep Networks to Encode Facial Appearance and Dynamics"; IEEE Transactions on Affective Computing, IEEE, USA, vol. 9, No. 4, pp. 578-584; XP011696768, DOI: 10.1109/TAFFC.2017.2650899; [gefunden am Nov. 26, 2018]; 2018.

European Office Action dated Nov. 29, 2019.

* cited by examiner

CLASSIFICATION BY MEANS OF RECORDINGS

PRIORITY STATEMENT

The present application hereby claims priority under 35 U.S.C. § 119 to European patent application number EP17163292.0 filed Mar. 28, 2017, the entire contents of which are hereby incorporated herein by reference.

FIELD

At least one embodiment of the invention generally relates to a method for classification by means or by way of recordings, a classification entity and/or a medical imaging modality.

BACKGROUND

Cancer illnesses, i.e. malignant tumor formations, are often accompanied by numerous changes in the external appearance of a patient. In the past, these changes have been detected only qualitatively by a medical practitioner in the context of a diagnosis, and therefore essentially reflect a sense of the physician for the state of health of the patient. The assessment of the external appearance in this case requires considerable medical experience, which can generally only be gained through many years of professional practice. In the case of practitioners with limited or no experience in particular, the risk of an incorrect assessment is therefore correspondingly high. Moreover, the purely qualitative assessment of the external appearance is only a poor and relatively inconclusive indicator of the actual state of health of the patient, and always reflects a personal and subjective impression of the examiner.

SUMMARY

At least one embodiment of the present invention allows for a more objective classification of the state of health of a patient on the basis of his or her external appearance.

At least one embodiment is directed to a method for classification; at least one embodiment is directed to a classification entity; and at least one embodiment is directed to a medical imaging modality.

At least one embodiment is directed to a method for classifying an examination object by way of recordings. The method includes: capturing at least one optical recording of the examination object; and determining and quantifying a number of defined characteristics of the examination object, on the basis of an analysis of the captured at least one optical recording with the aid of a machine learning method. The method further includes, effecting classification of the examination object, with respect to a classification criterion, based upon the quantified characteristics with the aid of a machine learning method.

For the purpose of classifying an examination object by way of recordings, the classification entity cited in the introduction has a capture unit, an analysis unit and a classification unit. In this way, it is so designed as to execute the method according to at least one embodiment of the invention for classifying an examination object. The analysis unit preferably comprises a determination unit and a quantification unit in this case. The determination unit in this case is preferably so designed as to evaluate the (optical) recordings of the examination object as part of the analysis and to identify defined characteristics therefrom as described above. The quantification unit is so designed as to quantify the defined characteristics after or concurrently with the determination.

At least one embodiment is directed to a method for classifying an examination object by way of recordings, comprising:
  capturing at least one optical recording of the examination object;
  capturing, by a medical imaging modality, at least one medical imaging data of an interior of the examination object;
  determining a number of characteristics of the examination object and quantifying the number of characteristics determined, based upon an analysis of the at least one optical recording and the at least one medical imaging data, with aid of a first machine learning method; and
  classifying the examination object, with respect to a classification criterion, based upon the quantified number of characteristics, with aid of at least one of the first machine learning method and a second machine learning method.

At least one embodiment is directed to a method for classifying an examination object by way of recordings, comprising:
  capturing at least one optical recording of the examination object;
  capturing, by a computed tomography device, at least one medical computed tomography imaging data of an interior of the examination object;
  determining a number of characteristics of the examination object and quantifying the number of characteristics determined, based upon an analysis of the at least one optical recording and the at least one medical computed tomography imaging data, with aid of a first machine learning method; and
  classifying the examination object, with respect to a classification criterion, based upon the quantified number of characteristics, with aid of at least one of the first machine learning method and a second machine learning method.

The medical imaging modality comprises a classification entity according to at least one embodiment of the invention. The medical imaging modality can be designed as an MRT (magnetic resonance tomography) system, angiography system, ultrasound system or PET (positron emission tomography) system, for example. However, it is preferably designed as a CT (computed tomography) system. The interaction of at least one embodiment of the inventive classification entity with the other components of the medical imaging modality is particularly advantageous in this case, since information about both the interior and the external appearance of the patient can be obtained in this way. This means that it is possible quantitatively to capture both the development of carcinomas during treatment and further external symptoms of the illness, for example.

The essential components of the classification entity according to at least one embodiment of the invention can be designed mainly in the form of software components. In principle, however, some of these components can also be realized in the form of software-assisted hardware, e.g. FPGAs or similar, in particular if particularly fast calculations are required. The required interfaces can likewise be designed as software interfaces, e.g. if data only has to be received from other software components. However, they can also be designed as hardware-based interfaces which are activated by suitable software.

In particular, the classification entity according to at least one embodiment of the invention can be part of a user terminal of a medical imaging modality.

A largely software-based realization has the advantage that even user terminals and/or computing units already in use can easily be upgraded by way of a software update in order to function in the inventive manner. In this respect, a corresponding computer program product comprises a computer program which can be loaded directly into a memory entity of a classification entity of a medical imaging modality, with program sections for executing all the steps of the inventive method when the program is executed in the classification entity. In addition to the computer program, such a computer program product may optionally comprise additional elements such as e.g. documentation and/or additional components, including hardware components such as e.g. hardware keys (dongles, etc.) for use of the software.

BRIEF DESCRIPTION OF THE DRAWINGS

The invention is explained again below in greater detail with reference to the appended figures and example embodiments. In this case, identical components are denoted by identical reference numerals in the different figures. The figures are generally not to scale.

DETAILED DESCRIPTION OF THE EXAMPLE EMBODIMENTS

Figure 1:
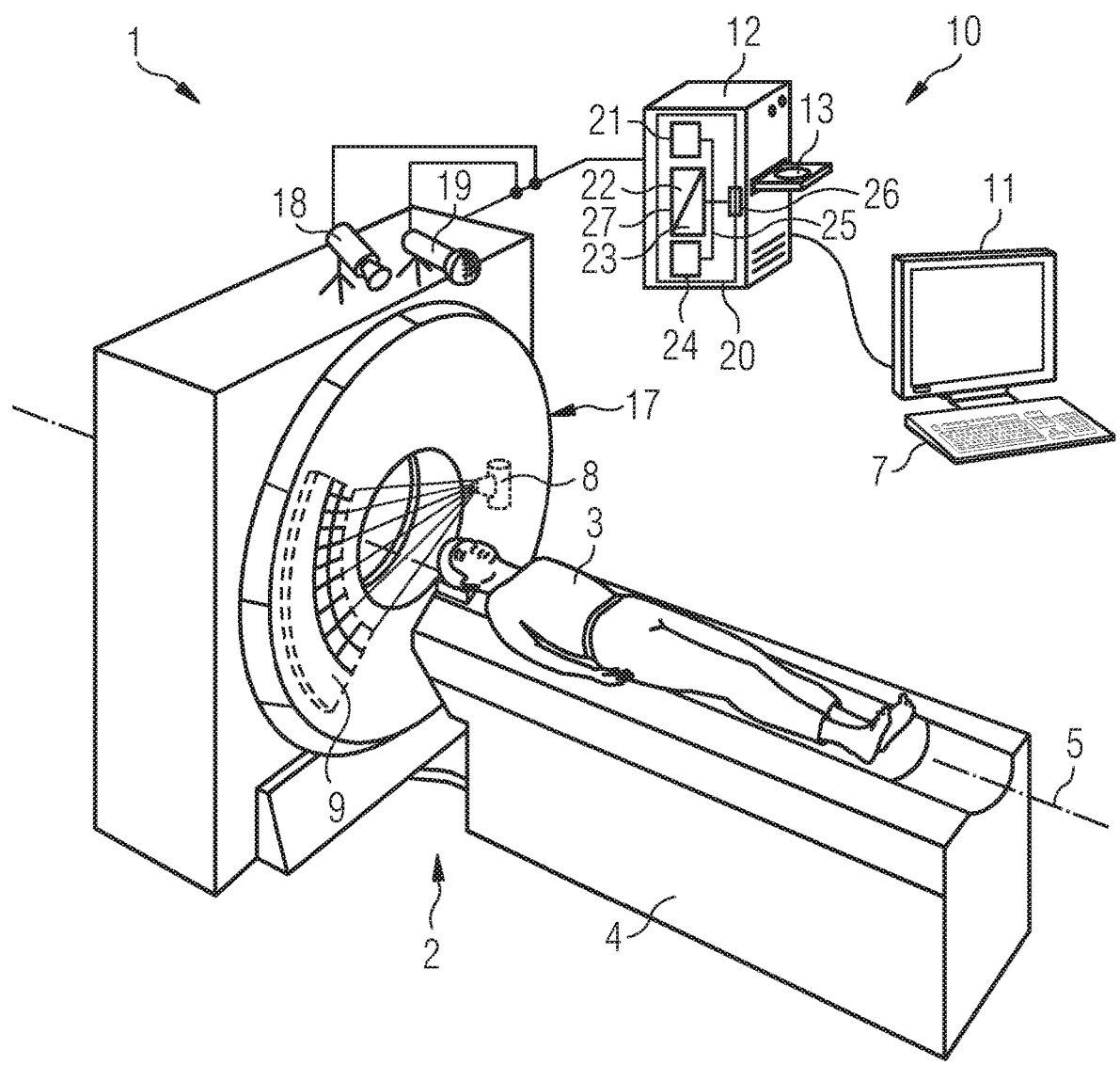
FIG. 1 shows a schematic view of an example embodiment of a medical imaging modality according to the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment is directed to a method for classifying an examination object by way of recordings. The method includes: capturing at least one optical recording of the examination object; and determining and quantifying a number of defined characteristics of the examination object, on the basis of an analysis of the captured at least one optical recording with the aid of a machine learning method. The method further includes, effecting classification of the examination object, with respect to a classification criterion, based upon the quantified characteristics with the aid of a machine learning method.

The classification is preferably effected automatically, i.e. at least semiautomatically and ideally fully automatically. It represents a categorization or assignment to a class, category or level. The examination object can be a patient in the form of an animal, for example, but is preferably a human patient. Therefore the terms "examination object" and "patient" are used synonymously in the following.

Optical recordings are considered to be any image recordings which are essentially acquired in the visible range of electromagnetic radiation, i.e. in a section of the light spectrum perceptible to the human eye and if applicable in the infrared and/or ultraviolet range. They are preferably made exclusively from outside the examination object, i.e. the recording devices do not penetrate into the interior of the examination object, i.e. into bodily orifices of the patient, for example. The recordings can be embodied as one or more still images in this case, but also as an image sequence, i.e. a video or film of the examination object. They may comprise both two-dimensional (2D) and three-dimensional (3D) recordings. The optical recordings may also comprise a combination of different recording methods, e.g. a high-resolution still image and a video of lower resolution. It is possible to optically capture the whole body of a patient in this way, for example, though individual body regions such as e.g. the face and/or the hands can also be captured separately if appropriate for the determination and/or quantification of the corresponding characteristic, as explained in greater detail below.

The recordings are subsequently analyzed, wherein further data, e.g. patient data such as age, weight, height, previous illnesses, etc., can also be included. Partial steps of the analysis, e.g. selecting a region or setting parameters, can be performed by an operator, but the analysis is preferably effected fully automatically by way of a machine learning method as described in greater detail below. As part of the analysis, depending on the machine learning method, it is feasible for individual characteristics to first be determined separately in one partial step and then quantified in a further partial step, though the determination and quantification can also be effected in a single step, i.e. concurrently and jointly or simultaneously.

As part of the analysis, distinctive topographical attributes can first be established as characteristics and then placed in relation to each other. For example, anatomical landmarks can be determined and evaluated in respect of their distance and/or arrangement. Furthermore, e.g. the extent or the volume of body parts, organs and/or extremities can be identified and contribute to the analysis. For example, body proportions can be determined and evaluated in relation to each other. It is alternatively or additionally possible in this case to undertake a color capture, in particular of the skin color or the conjunctiva color.

The quantification of the characteristics signifies a representation of the characteristic as a numerical value. This can be effected using e.g. absolute parameters or relative parameters in this case, depending on the respective characteristic. For example, measurable variables such as length, thickness, volume, shape, geometric arrangement, etc. of body parts and/or organs of the patient can be captured as absolute parameters. With the aid of video recordings, it is possible in a further example to measure the time between breaths or cough movements (and/or the frequency thereof, depending on the respective application) as absolute parameters. The absolute parameters can therefore generally be directly quantified. In this case, however, different parameters can also be placed in a ratio with each other and therefore evaluated as new parameters, possibly relating to another characteristic. For example, the color can be measured as an absolute parameter or measured in a ratio. In the case of color values measured as absolute parameters, the analysis is preferably implemented directly on the basis thereof. Otherwise, for example, the colors of different body regions of the patient are placed in a ratio with each other.

Relative parameters, e.g. a relative measure of the confusion of the patient, cannot generally be measured directly. In this case, the corresponding characteristics can be assessed e.g. by way of a complex analysis of the overall appearance of the patient. They are therefore quantified e.g. by way of a rating on a scale or with reference to a rating benchmark. Unlike the previous assessment by a physician, this means that the (possibly abstract) characteristics are inventively transformed into parameters with assigned parameter values by way of the quantification, and can therefore be measured and/or evaluated.

The classification signifies a complex combined view based on an evaluation of the quantified characteristics in respect of the classification criterion. Depending on the classification criterion, the individual characteristics may be variously weighted or placed in various dependencies with each other, for example. For example, this means that if a defined pair of characteristics or a defined group of characteristics is particularly prevalent, it is also particularly relevant for the classification.

The classification criterion is preferably a defined clinical picture in this case. This means that the classification preferably specifies whether or not the clinical picture applies to the patient. The classification is also effected with the aid of a machine learning method. In this case, a first machine learning method can be used for the analysis, i.e. the determination and/or the quantification of the characteristics, and a second machine learning method, this differing from the first, can be used for the classification. It is also possible to use different machine methods as required for different characteristics that must be determined and quantified. It is however also possible partly or wholly to use the same machine learning method depending on the respective application. The inventive method thereby allows a more objective, simpler and faster categorization in respect of the classification criterion.

For the purpose of classifying an examination object by way of recordings, the classification entity cited in the introduction has a capture unit, an analysis unit and a classification unit. In this way, it is so designed as to execute the method according to at least one embodiment of the invention for classifying an examination object. The analysis unit preferably comprises a determination unit and a quantification unit in this case. The determination unit in this case is preferably so designed as to evaluate the (optical) recordings of the examination object as part of the analysis and to identify defined characteristics therefrom as described above. The quantification unit is so designed as to quantify the defined characteristics after or concurrently with the determination.

The medical imaging modality comprises a classification entity according to at least one embodiment of the invention. The medical imaging modality can be designed as an MRT (magnetic resonance tomography) system, angiography system, ultrasound system or PET (positron emission tomography) system, for example. However, it is preferably designed as a CT (computed tomography) system. The interaction of at least one embodiment of the inventive classification entity with the other components of the medical imaging modality is particularly advantageous in this case, since information about both the interior and the external appearance of the patient can be obtained in this way. This means that it is possible quantitatively to capture both the development of carcinomas during treatment and further external symptoms of the illness, for example.

The essential components of the classification entity according to at least one embodiment of the invention can be designed mainly in the form of software components. In principle, however, some of these components can also be realized in the form of software-assisted hardware, e.g. FPGAs or similar, in particular if particularly fast calculations are required. The required interfaces can likewise be designed as software interfaces, e.g. if data only has to be received from other software components. However, they can also be designed as hardware-based interfaces which are activated by suitable software.

In particular, the classification entity according to at least one embodiment of the invention can be part of a user terminal of a medical imaging modality.

A largely software-based realization has the advantage that even user terminals and/or computing units already in use can easily be upgraded by way of a software update in order to function in at least one embodiment of the inventive manner. In this respect, a corresponding computer program product comprises a computer program which can be loaded directly into a memory entity of a classification entity of a medical imaging modality, with program sections for executing all the steps of at least one embodiment of the inventive method when the program is executed in the classification entity. In addition to the computer program, such a computer program product may optionally comprise additional elements such as e.g. documentation and/or additional components, including hardware components such as e.g. hardware keys (dongles, etc.) for use of the software.

For the purpose of transportation to the classification entity and/or for the purpose of storage on or in the classification entity, it is possible to use a computer-readable medium such as e.g. a memory stick, a hard disk or other transportable or integral data medium on which are stored the executable program sections of the computer program which can be read in and executed by a computing unit of the classification entity. For this purpose, the computing unit may have e.g. one or more interworking microprocessors or the like.

Further particularly advantageous embodiments and developments of the invention are derived from the claims and the following description, wherein the claims of one statutory class of claim can be developed in a similar manner to the claims or description parts of another statutory class of claim, and in particular individual characteristics of different example embodiments or variants can also be combined to form new example embodiments or variants.

The examination object is preferably classified in respect of a cancer illness. This means that a cancer illness, i.e. malignant tissue regeneration or a malignant tumor, is preferably used as a classification criterion. The cancer illness in respect of which the classification is to take place is most preferably lung cancer. This often occurs in combination with the symptoms described below.

Using a method according to at least one embodiment of the invention, the defined characteristics that are to be determined and quantified preferably comprise at least one characteristic from the following list: pale conjunctiva, jaundice, clubbing of the fingers, Horner's syndrome, Cushing's syndrome, persistent coughing, hemoptysis, breathlessness, dysphagia, confusion, anorexia, tiredness and/or ascites.

Clubbing of the fingers signifies a swelling or thickening of fingers and toes in this case. Horner's syndrome is a specific form of nerve damage caused by a failure in the top part of the sympathetic nervous system. It has a three-part complex of symptoms which usually occurs unilaterally and consists of pupil contraction, drooping upper eyelid and an eyeball which is slightly sunken into the eye socket. Cushing's syndrome customarily signifies bodily changes which are caused by a high cortisol level in the blood, wherein increased fatty tissue typically accumulates at the body trunk and the limbs become thinner due to muscle wastage. The other characteristics listed are also symptomatically known. Thus hemoptysis signifies expectoration of blood, dysphagia signifies difficulty in swallowing, ascites signifies peritoneal edema and anorexia signifies loss of appetite.

In this context, some characteristics can be measured absolutely in parameter values, e.g. the volume of fingers and toes in the case of the "clubbing of the fingers" characteristic. Other characteristics can be determined and quantified in comparison with other body regions, e.g. by comparing the halves of the face in the case of Horner's syndrome. In the case of other characteristics again, e.g. the confusion or bewilderment of the patient, a complex analysis of the optical and possibly acoustic recordings is required.

In principle, any desired characteristics from the list can contribute to the classification. This means that, for example, only a selected group of characteristics can be used if required. However, the classification is ideally effected using all of the characteristics cited in the list.

Using a method according to at least one embodiment of the invention, provision is preferably made for additionally capturing a number of acoustic recordings of the examination object, The acoustic recordings also being used for the classification. The acoustic recordings can be captured by way of a microphone, for example. Their additional use advantageously facilitates the determination and quantification of persistent coughing and/or breathlessness, for example.

The acoustic recordings are ideally analyzed by way of voice analysis. They can provide information about the bewilderment of the patient, for example, if unconnected words or incoherent utterings (continuous muttering) are captured. Their use for the classification therefore preferably means that the method steps implemented as described above for the optical recordings are also implemented for the acoustic recordings.

In the case of a method according to at least one embodiment of the invention, the machine learning methods preferably comprise at least one of the following algorithms: support vector machines, Bayesian classifiers, k-means clustering, deep belief networks, deep residual learning, reinforcement learning, decision trees, recurrent neural networks, inductive programming or preferably convolutional neural networks. The cited algorithms and the way in which they function respectively are known from the following publications, the entire contents of each of which are hereby fully incorporated herein by reference:

"An Introduction to Machine Learning", Miroslav Kubat, Springer;
"Deep Learning", Goodfellow, Bengio, Courville, MIT Press;
"Machine learning: Trends, perspectives, and prospects", Jordan, Mitchell, Science 2015(349) 255.

Before implementing a method according to at least one embodiment of the invention, the algorithm or algorithms are preferably prepared with the aid of a training process. In this way, on the basis of training data that is stored or supplied and was acquired from previous patients, the algorithms learn how the defined characteristics are determined and/or quantified. At the same time or separately, they learn how the classification in respect of the classification criterion is then performed on the basis of the analysis of these characteristics. If necessary, the determination and quantification of an individual characteristic can also be learned separately if stock data and/or standard images (stock photography) are available for this characteristic.

The training or the training process is preferably continued iteratively with repeated implementation of at least one embodiment of the inventive method (inline machine learning), such that the results of the method improve continuously with the increase in the number of method implementations and the number of examination objects classified. The training data and classification data is preferably exchanged, e.g. via a network (cloud), between different examination sites and/or different medical imaging modalities operating in accordance with the invention. An acceleration of the learning process and consequently a faster improvement of the inventive classification is advantageously achieved thereby. In order to achieve this, an assessment and/or rating of the classification can ideally be performed by an operator as part of the training (i.e. also after every implementation of the inventive method) and used as feedback for the training in order to improve the results.

In the case of a method according to at least one embodiment of the invention, a probability of a correct classification is preferably also determined in addition to the classification. This means that, in addition to the classification per se, an analysis preferably also determines the degree of reliability in respect of correct classification. The probability can also be output as a value in this case, wherein this can be e.g. a confidence range and/or a percentage. This advantageously achieves not only a more objective classification, but also indicates how trustworthy the classification is to be considered.

As mentioned in the introduction, particular synergetic effects are produced when both the external appearance of a patient and data from his or her interior are assessed in respect of the classification criterion. Therefore the inventive method is preferably linked to an examination by way of a medical imaging modality which ideally captures data from the interior of the examination object. The examination can be a medical computed tomography imaging examination in particular. The imaging modality can be a computed tomography device in particular.

The optical recordings are preferably made using a 2D camera, a 2D RGB camera and/or a 3D camera. Depending on the requirements, it is possible in this case to use economical and commercially available cameras and sensors, or high-quality models which acquire comparatively better data and therefore also allow a better analysis. The cameras can therefore be used to capture e.g. grayscale values or color values of the examination object, though it is also possible to acquire false-color recordings such as e.g. infrared images, or a spatial impression or a distance measurement by way of a 3D camera. A 3D camera is intended in this case to signify different systems such as e.g. a stereo camera, a TOF camera (time of flight) or even a triangulation system which measures distortions of a defined light pattern on the examination object.

The determination of the defined characteristics preferably comprises the use of a face recognition algorithm. Face recognition in this case signifies an analysis of the configuration of visible characteristics in the frontal head region of the patient, established by geometric arrangement and textural attributes of the surface. Such algorithms are already developed in detail, freely available (open source) and resource-efficient, and can therefore advantageously be deployed in the context of the inventive method.

At least one embodiment of the inventive method is preferably used to determine the change of the examination object in respect of the classification criterion between a first examination and at least one subsequent examination. It is thereby possible e.g. to document the history of the illness and/or the response to a specific therapy in a patient. In particular, the changes of the characteristics in the time period between the examinations can be analyzed in relation to each other in this case. This means that the characteristics during the subsequent examinations can be assessed or quantified in relation to the first examination.

FIG. 1 shows an example and simple schematic view of a computed tomography system 1 as a medical imaging modality 1 according to an embodiment of the invention, comprising a user terminal 10 and a computed tomography device 2. The computed tomography system 1 is designed to execute an embodiment of the inventive method for classification. The computed tomography device 2 comprises a patient couch 4, which supports a patient 3 as an examination object 3 and can be repositioned along a system axis 5. In the following, the system axis 5 is also referred to as the z-axis, along which the patient 3 can be positioned in the measuring field. It further comprises a gantry 17 with a source-detector arrangement 8, 9, this being rotatably mounted about the system axis 5. The source-detector arrangement 8, 9 has an x-ray source 8 and a detector 9, these being aligned opposite to each other in such a way that x-radiation coming from the focus of the x-ray source 8 strikes the detector 9 during operation. The way in which such a CT device 2 functions is generally known and is therefore not explained further here.

The computed tomography system 1 also comprises a camera 18, e.g. a 3D stereo camera (schematically illustrated here) for the acquisition of three-dimensional optical recordings A1 and a microphone 19 for the acquisition of acoustic recordings A2. The user terminal 10 comprises a computing unit 12, a display unit 11, e.g. a screen, and an input unit 7, e.g. a keyboard, for capturing user inputs. The computing unit 12 comprises a classification entity 20 according to an embodiment of the invention and a drive 13 for reading a computer-readable medium according to the invention. The classification entity 20 is designed to execute an embodiment of the inventive method in this case. The result of an embodiment of the inventive method, i.e. the classification, can be represented on the display unit 11, for example, and/or stored in a memory and/or transmitted to other systems. This means that the classification can be used for a subsequent diagnosis by medical personnel, as a comparison for subsequent examinations and/or for the purpose of training a machine learning method.

The classification entity 20 is shown by way of example in a block schematic diagram. It comprises an interface 26, a capture unit 21, an analysis unit 27 with a determination unit 22 and a quantification unit 23, and a classification unit 24, these being connected by way of a bus 25 for the purpose of data transfer. Therefore data can be freely exchanged between the components of the analysis unit 27 via the bus 25. The interface 26 provides a connection between the classification entity 20 and e.g. a network, memory entities and/or other components of the CT system 1 such as e.g. the 3D camera 18 and the microphone 19. It is used to transfer data from these components to the classification entity 20 and also vice versa if applicable.

Figure 2:
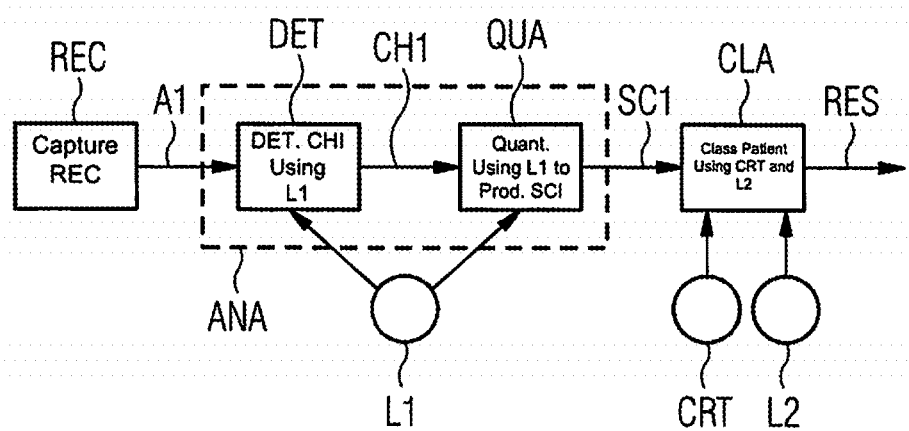
FIG. 2 shows a block diagram of an example embodiment of a method for classification according to the invention.

FIG. 2 shows an example embodiment of a method for classification according to the invention in a block schematic representation. In one step REC, three-dimensional optical recordings A1 (e.g. 3D video recordings) of the patient 3 are captured by way of the stereo camera 18 and transferred via the interface 26 of the classification entity 20 to the capture unit 21 thereof, where they are stored temporarily, for example. In a next step ANA, which is divided here into two substeps DET, QUA, the captured data or the recordings A1 are evaluated in the analysis unit 27 with the aid of a machine learning method L1 (e.g. "convolutional neural networks" here) which has previously been trained on the basis of other patient data and/or patient recordings.

The substeps DET, QUA of the analysis ANA in this case may engage with each other or be closely interlinked if applicable, depending on the defined characteristic CH1 concerned. The defined characteristics CH1, CH2, CH3, . . . are briefly described below with reference to FIG. 4.

Figure 4:
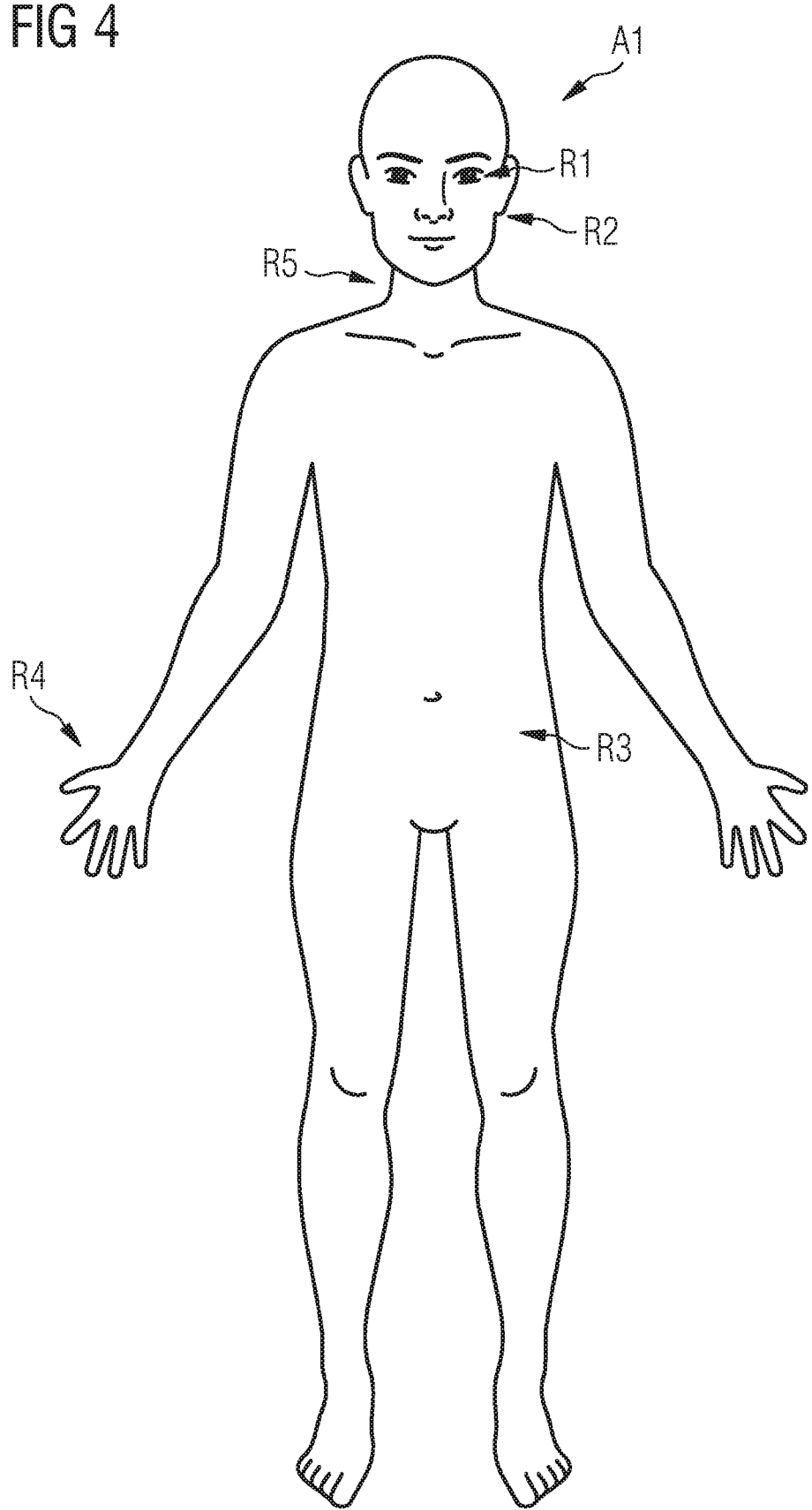
FIG. 4 shows a schematic view of an optical recording of an examination object.

FIG. 4 schematically represents an optical recording A1 of a frontal view of a patient 3. The patient has a number of body regions R1, R2, . . . , R5, wherein the body regions R1, R2, . . . , R5 can vary in relevance for the analysis of a characteristic. For example, in order to determine and quantify the characteristics "pale conjunctiva" and "Horner's syndrome", provision is essentially made for analyzing an eye region R1 of the patient 3, wherein e.g. absolute color matching is performed in order to establish and rate the pale conjunctiva, and both halves of the face are compared with each other for Horner's syndrome. In respect of the characteristic "jaundice", e.g. a face color can be analyzed in a face region R2, i.e. including the eye region R1 and in particular the sclera of the eye here. For the analysis of the characteristic "clubbing of the fingers", a hand region R4 is considered in particular, and the volume or spatial dimensions of fingers and hands are assessed here and e.g. placed in relation to a bodyweight of the patient 3.

In order to analyze the characteristic "ascites", e.g. a stomach size or a volume of the stomach of the patient is determined in a stomach region R3 and rated in relation to the other body measurements of the patient. The characteristic "anorexia" can be analyzed in a similar manner, wherein overall consideration of the recordings A1 of the patient 3 can also provide information about emaciation and contribute to the analysis here.

The characteristics "dysphagia", "persistent coughing" and "hemoptysis" can be determined and quantified e.g. by way of analyzing a neck region R5, wherein time-relative observation of the neck region R5 in respect of irregular sequences of movement here can provide the necessary information. In the case of hemoptysis, the color of the expectoration can also be taken into consideration. In addition, acoustic recordings A2 of the patient 3 can also be used for the purpose of analyzing these characteristics, as explained in greater detail below.

Determination and/or rating of the characteristic "Cushing's syndrome" can be performed e.g. by analysis of the geometric shapes in the face region R2 and the neck region R5 of the patient. For the characteristics "breathlessness", "confusion" and "tiredness", an overall contemplation of all body regions R1, R2, . . . , R5 of the patient 3 may be required, since the appearance and/or the behavior of the patient overall is significant here.

In summary, the defined characteristics can therefore be determined and/or quantified e.g. by analyzing the length, the thickness, the volume, the shape, the geometric arrangement and the color of regions of the patient body, or also in a combined view or a time-relative change of these parameters. A combination of the optical recordings A1 with acoustic recordings is also suitable for the analysis in the case of some defined characteristics.

This complex analysis is made possible in particular by virtue of the use of a machine learning method L1 (see FIG. 2). In this case, a defined characteristic CH1 can initially be determined in the determination unit 22 in a first intermediate step DET and then quantified in the quantification unit 23 in a further intermediate step QUA. However, the determination DET and the quantification QUA can also be effected simultaneously in a single analysis step ANA. Determination unit 22 and quantification unit 23 can be designed together in one unit accordingly. As a result of the analysis ANA, at least one quantified characteristic SC1 is obtained in any case.

On the basis of the quantified characteristic SC1, in a subsequent step CLA the patient 3 is classified in respect of a classification criterion CRT, e.g. in respect of a lung cancer illness. The classification CLA is effected using a second machine learning method L2 in this case, wherein "convolutional neural networks" are preferably used here again. A result RES of the classification CLA, e.g. the categorization for or against a lung cancer illness, can be output e.g. on the screen 11 of the user terminal 10 or stored in a memory entity and/or a network, these being connected to the classification entity 20.

Figure 3:
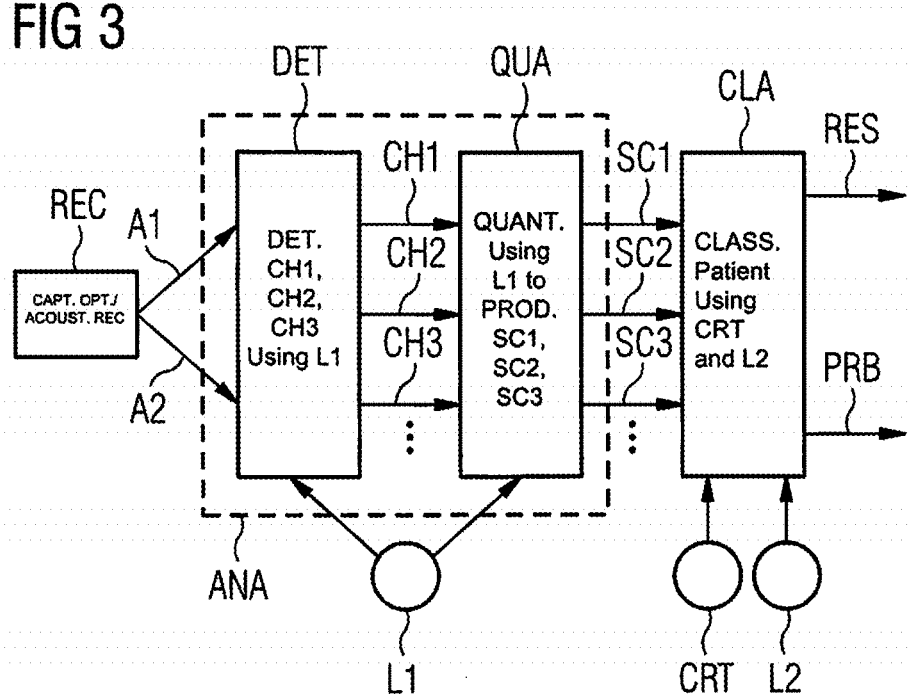
FIG. 3 shows a block diagram of a further example embodiment of a method for classification according to the invention.

The example embodiment of an inventive method for classification as illustrated in block schematic form in FIG. 3 is essentially similar to the method described with reference to FIG. 2. However, it differs in that both optical recordings A1 and acoustic recordings A2 of the patient 3 are captured. These recordings A1, A2 are used in the following analysis step ANA as a basis for determining and quantifying defined characteristics CH1, CH2, CH3, . . . , wherein the acoustic recordings A2 are also used for the analysis in addition to the optical recordings A1 in this step. This complex analysis is likewise preferably effected using "convolutional neural networks" as a machine learning method L1. A quantified characteristic SC1, SC2, SC3, . . . is generated for each defined characteristic CH1, CH2, CH3, . . . by way of the analysis, as described above for the individual characteristics with reference to FIG. 4.

On the basis of the quantified characteristics SC1, SC2, SC3, . . . , both a result RES of the classification CLA, i.e. the classification per se, and a probability PRB for the correctness of the classification, e.g. a confidence range, are determined in the classification step CLA following thereupon. Since the evaluation of the quantified characteristics SC1, SC2, SC3, requires a complex rating in its combined view, "convolutional neural networks" are preferably used again as a second machine learning method L2 for the classification CLA. In this case, the individual quantified characteristics can be variously weighted and/or placed in complex dependencies with each other, for example. For example, a characteristic may be completely ignored if another characteristic is situated within a specific value range and/or characteristics may have a stronger influence on the classification if they occur together.

The results RES, PRB obtained by way of an embodiment of the inventive method may in themselves already provide an indicator for a diagnosis by a medical practitioner, but they are preferably used in combination with the results obtained from an examination or imaging that has been performed using the medical imaging modality 1, i.e. the CT system 1. The results can also be stored in a memory and thereby document the history of the illness or the success of a therapy. Overall, an embodiment of the inventive method allows a more objective evaluation of the external appearance of the patient in respect of the illness concerned.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

In conclusion, it is again noted that the apparatus and methods described in detail above are merely example embodiments which can easily be modified by a person skilled in the art without thereby departing from the scope of the invention. Furthermore, the use of the indefinite article "a" or "an" does not exclude multiple occurrences of the features concerned. Likewise, the terms "entity", "unit" and "system" do not preclude the respective component consisting of multiple interworking subcomponents, which may also be physically distributed if applicable. For example, a CT device and a classification entity of a medical imaging modality according to the invention may be arranged in a single room, but they may also be connected to each other over great distances via a network.

What is claimed is:

1. A method for classifying an examination object by way of recordings, comprising:
   capturing at least one optical recording of the examination object;
   determining a number of characteristics of the examination object and quantifying the number of characteristics determined, based upon an analysis of the at least one optical recording, with aid of a first machine learning method; and
   classifying the examination object, with respect to a classification criterion, based upon the quantified number of characteristics, with aid of at least one of the first machine learning method and a second machine learning method.

2. The method of claim 1, wherein the classification criterion is a cancer illness, and wherein the classifying includes classifying the examination object with respect to the cancer illness.

3. The method of claim 2, wherein the cancer illness is lung cancer.

4. The method of claim 3, wherein the number of characteristics include at least one characteristic including: pale conjunctiva, jaundice, clubbing of fingers, Horner's syndrome, Cushing's syndrome, persistent coughing, hemoptysis, breathlessness, dysphagia, confusion, anorexia, tiredness and ascites.

5. The method of claim 1, wherein a number of acoustic recordings of the examination object are captured during the capturing and wherein the number of acoustic recordings are used for the classifying.

6. The method of claim 5, further comprising determining a probability of a correct classification.

7. The method of claim 5, wherein the at least one optical recording of the examination object is captured by a medical imaging modality.

8. The method of claim 5, wherein the capturing of the at least one optical recording is made with the aid of at least one of a 2D camera, a 2D RGB camera and a 3D camera.

9. The method of claim 5, wherein the determining of the number of characteristics includes use of a face recognition algorithm.

10. A non-transitory memory entity of a classification entity of a medical imaging modality, storing a computer program including program sections for executing the method of claim 5 when the computer program is executed in the classification entity of the medical imaging modality.

11. A non-transitory computer-readable medium storing program sections, readable and executable by a computing unit to execute the method of claim 5 when the program sections are executed by the computing unit.

12. The method of claim 1, wherein the at least one of the first machine learning method and second machine learning method includes at least one of an algorithm for: support vector machines, Bayesian classifiers, k-means clustering, deep belief networks, deep residual learning, reinforcement learning, decision trees, recurrent neural networks, inductive programming and convolutional neural networks.

13. The method of claim 1, further comprising determining a probability of a correct classification.

14. The method of claim 1, wherein the at least one optical recording of the examination object is captured by a medical imaging modality.

15. The method of claim 1, wherein the capturing of the at least one optical recording is made with aid of at least one of a 2D camera, a 2D RGB camera and a 3D camera.

16. The method of claim 1, wherein the determining of the number of characteristics includes use of a face recognition algorithm.

17. A non-transitory computer program product including a computer program, directly loadable into a memory entity of a classification entity of a medical imaging modality, the computer program including program sections for executing the method of claim 1 when the computer program is executed in the classification entity of the medical imaging modality.

18. A non-transitory computer-readable medium storing program sections, readable and executable by a computing unit to execute the method of claim 1 when the program sections are executed by the computing unit.

19. A classification entity for classifying an examination object by way of recordings, comprising
   a camera, designed to capture optical recordings of the examination object; and
   at least one processor,
      designed to determine and quantify characteristics of the examination object based upon an analysis of the optical recordings captured by the camera, with aid of a first machine learning method, and
      designed to classify the examination object with respect to a classification criterion, based upon the characteristics quantified, with aid of at least one of the first machine learning method and a second machine learning method.

20. A medical imaging modality comprising the classification entity of claim 19.

21. A method for classifying an examination object by way of recordings, comprising:
- capturing at least one optical recording of the examination object;
- capturing, by a medical imaging modality, at least one medical imaging data of an interior of the examination object;
- determining a number of characteristics of the examination object and quantifying the number of characteristics determined, based upon an analysis of the at least one optical recording and the at least one medical imaging data, with aid of a first machine learning method; and
- classifying the examination object, with respect to a classification criterion, based upon the quantified number of characteristics, with aid of at least one of the first machine learning method and a second machine learning method.

22. A non-transitory memory entity of a classification entity of a medical imaging modality, storing a computer program including program sections for executing the method of claim 21 when the computer program is executed in the classification entity of the medical imaging modality.

23. A non-transitory computer-readable medium storing program sections, readable and executable by a computing unit to execute the method of claim 21 when the program sections are executed by the computing unit.

24. A method for classifying an examination object by way of recordings, comprising:
- capturing at least one optical recording of the examination object;
- capturing, by a computed tomography device, at least one medical computed tomography imaging data of an interior of the examination object;
- determining a number of characteristics of the examination object and quantifying the number of characteristics determined, based upon an analysis of the at least one optical recording and the at least one medical computed tomography imaging data, with aid of a first machine learning method; and
- classifying the examination object, with respect to a classification criterion, based upon the quantified number of characteristics, with aid of at least one of the first machine learning method and a second machine learning method.

25. A non-transitory memory entity of a classification entity of a medical imaging modality, storing a computer program including program sections for executing the method of claim 24 when the computer program is executed in the classification entity of the medical imaging modality.

26. A non-transitory computer-readable medium storing program sections, readable and executable by a computing unit to execute the method of claim 24 when the program sections are executed by the computing unit.

* * * * *